(12) United States Patent
Wright

(10) Patent No.: US 6,254,616 B1
(45) Date of Patent: *Jul. 3, 2001

(54) SUTURE CONTAINER

(75) Inventor: Alastair Douglas Wright, South Queensferry (GB)

(73) Assignee: Ethicon, Inc., Somerville, NJ (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/257,313

(22) Filed: Feb. 25, 1999

(51) Int. Cl.[7] .................................................. A61B 17/04
(52) U.S. Cl. ............................................................. 606/146
(58) Field of Search .................................... 606/146, 145; 242/134; 206/389

(56) References Cited

U.S. PATENT DOCUMENTS

| 3,901,244 | * | 8/1975 | Schweizer | 606/145 |
| 3,959,947 | | 6/1976 | Sommino | 53/21 |
| 4,084,692 | | 4/1978 | Bilweis | 206/403 |
| 5,131,534 | | 7/1992 | Brown et al. | 206/63.3 |
| 5,156,311 | * | 10/1992 | Spencer, Jr.et al. | 255/41 |

FOREIGN PATENT DOCUMENTS

| 0 557 993 A1 | 12/1994 | (EP) | A61B/17/06 |
| 1 369 178 | 2/1974 | (GB) | B65D/75/30 |

* cited by examiner

Primary Examiner—Henry J. Recla
Assistant Examiner—Vy Q. Bui
(74) Attorney, Agent, or Firm—Emil Richard Skula

(57) ABSTRACT

A suture container having a spool rotatably mounted therein. A length of suture material is wound on the spool is wrapped in an outer bacterial-proof envelope.

1 Claim, 3 Drawing Sheets

SUTURE CONTAINER

The present invention relates to a suture container, and particularly a contain comprising a spool onto which a length of suture material may be wound and then sterilized and packaged for sale. The suture container is particularly suitable for use by veterinary surgeons.

Veterinary surgeons have traditionally used catgut for suturing. It has been the practice to supply a substantial length (e.g. 50 meters) of catgut wound onto a spool in a contained filled with alcohol, usually isopropanol. One end of the suture protrudes through an orifice in a rubber septum, so that the veterinary surgeon can withdraw the desired length of suture from the spool, while maintaining sterility within the container.

More recently, the move has been towards synthetic sutures, and particularly absorbable sutures formed from biodegradable lactide/glycolide polymers such as Vicryl® polymer. The traditional dispensers are now in use for absorbable sutures, but there are a number of disadvantages. In particular, there is a risk that moisture will enter the dispenser, leading to degradation of the polymer. Partial degradation of a length of suture material will substantially reduce its tensile strength, but this may not be apparent merely from visual inspection of the suture. Accordingly, the tissue of the patient may be ligated with unsuitable suture material, and the suture may break down before the tissue heals. Also, the known containers are cumbersome and relatively heavy.

It is the object of the present invention to provide a suture container that avoids the above disadvantages.

According to the present invention, there is provided a suture container having a spool rotatably mounted therein, and a length of suture material wound on said spool, said container being wrapped in an outer bacteria-proof envelope. Preferably, the container comprises a first portion and a second portion, and the spool is rotatably mounted between the first and second portions. The first and second portions may be hingedly attached to each other. In a particularly preferred embodiment, the first and second portions are hingedly attached for relative movement about an axis which is parallel to the axis of rotation of the spool. However, it will be appreciated that the first and second portions may be attached to each other in a variety of alternative ways.

The container is preferably made from a plastics material, such as polypropylene, high density polyethylene (HDPE) or low density polyethylene (LDPE). Polypropylene is particularly preferred.

The spool may comprise a hub and two discs mounted thereon. Suture material, preferably up to about ten meters long, and more usually between 2 and 6 meters long, may be wound onto the hub between the two discs. The discs are preferably made from a plastics material, so as to minimize friction between the suture material and the discs when the suture is wound onto or withdrawn from the spool. Suitable plastics include polyvinylchloride and polyethylene terephthalate G. In general, the discs will be between 0.1 and 0.8 mm thick, and preferably between 0.25 and 0.6 mm thick. For example, the discs may be 0.3 or 0.5 mm thick.

It is particularly preferred that the discs be transparent or translucent. The expression "transparent or translucent", as used herein, is intended to cover discs which are sufficiently transparent or translucent for the suture material to be discernible through the discs. This has two particular advantages. Firstly, it is of assistance during assembly of the containers for sale, because it allows the operator to check than an appropriate amount of suture material has been properly wound onto the spool. Secondly, when the container itself is also transparent or translucent, or suitable apertures are provided in the sides of the container, it allows the user to judge how much suture material remains on the spool.

Although transparent plastic discs are preferred, it is also possible to form the discs from card, such as Invercote S, Cropper Board or Monadock card. In such a case, it may be desirable to provide the card with a reduced friction coating, such as a coating of polytetrafluoroethylene (PTFE).

In a preferred embodiment, the hub is provided with means for receiving one end of a length of suture material, to assist in winding the suture material onto the spool. Such means preferably comprises a slot or groove, and more particularly a slot arranged orthogonal to the axis of rotation of the hub.

The suture is preferably bioabsorbable, and may be made from lactide/glycolide polymer. Alternatively, however, the suture may be non-absorbable. For some surgical applications, a suture formed from stainless steel wire may be appropriate.

The bacterial-proof envelope may be made from any suitable material, such materials being well-known in the suture packaging art. Preferably, the envelop is formed from an aluminized plastics laminate, such as a Surlyn or Mylar foil. Most preferably, the bacterial-proof envelope is heat-sealed around its periphery, but adhesives may alternatively be used.

The suture container and suture are preferably sterilized using ethylene oxide, as is conventional with sutures intended for human use. However, alternative sterilization techniques may also be used, including γ-irradiation and autoclaving, provided that suitably resistant materials are chosen for the suture and the components of the container.

The suture container with a length of suture material wound on the spool will generally be placed inside the envelope prior to sterilization. If a gaseous sterilization medium such as ethylene oxide is being used, the envelope is of course left unsealed until after sterilization. Moreover, the container is preferably provided with a number of apertures in the walls thereof, to increase exposure of the suture material to the gaseous sterilant.

If ethylene oxide is used for sterilization, the suture and the container are first subjected to a pre-humidification step. A cardboard insert may be included in the envelope to absorb moisture during pre-humidification, and to retain moisture during exposure to ethylene oxide. The cardboard insert may be attached to the suture container, and it may bear graphical or textual material, such as instructions for use of the suture.

A suture container according to the present invention provides a conveniently small and sterile package from which a require length of suture material may be taken by a veterinary surgeon. Since, in the preferred embodiment, a comparatively short length of suture material is contained on the spool, it is anticipated that the container will be used on a disposable basis, i.e. once the container has been opened, the required amount of suture is used, and the container is then discarded. In this way, there is no risk of premature breakdown of the suture material due to storage of an opened container in an unsuitable environment.

The present invention is described with reference to the accompanying drawings in which.

Figure 1:
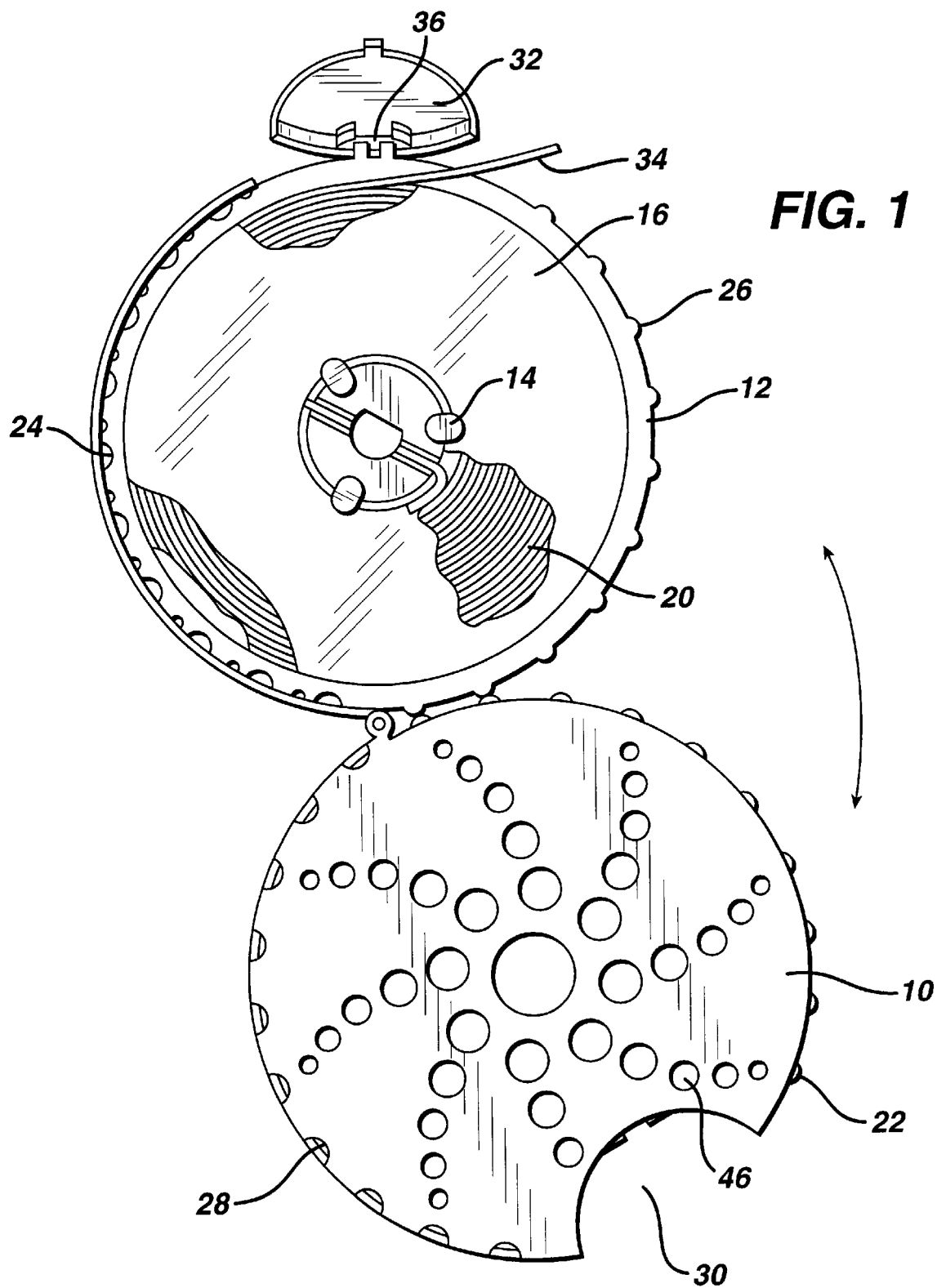
FIG. 1 is a plan view of an open suture container according to the present invention.
Figure 2:
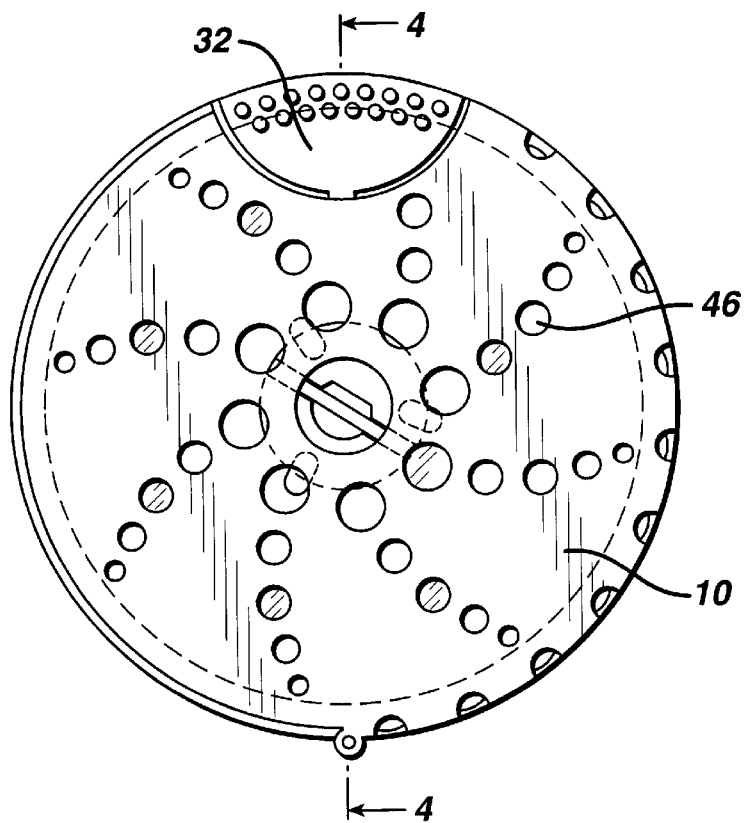
FIG. 2 is a plan view of a first portion of the container of FIG. 1.
Figure 3:
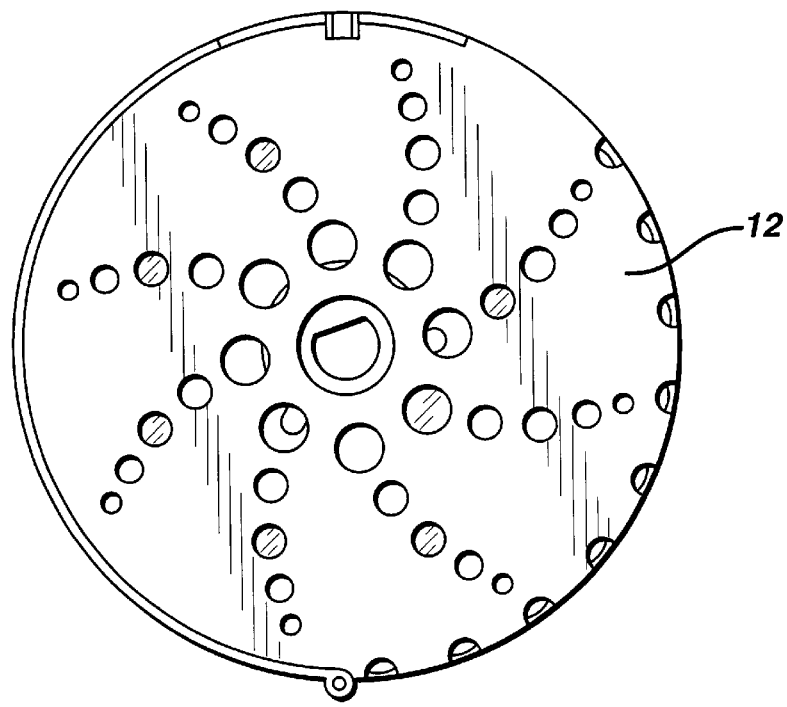
FIG. 3 is a plan view of a second portion of the container of FIG. 1.

Referring to FIGS. 1 to 4, there is shown a container comprising a first portion 10 and a second portion 12 which are hingedly attached together. Rotatably mounted within the container is a plastics spool comprising a hub 14, to which are fitted two transparent plastic discs 16, 18. Suture material 20 (approximately 5 meters) is wound onto the spool 14 in a gap 17 between the two discs 16, 18. The first and second portions 10, 12 of the container body are each provided with respective lugs 22, 26 and respective cut-outs 24, 28. The lugs 22, 26 are formed on the periphery of one side of the first and second portions 10, 12 such that they can engage with the cut-outs 24, 28 formed in the periphery of the other side of the first and second portions 10, 12. Thus, upon hingedly bring the two portions 10, 12 together, the lugs 22, 26 and cut-outs 24, 28 come into engagement with one another. The spool 14 and suture material 20 wound between the discs 16, 28 are thus securely closed within the container.

Access to the suture material 20 is provided via a cut-away region 30 in the first portion 10. This cut-away portion 30 may be closed by a correspondingly shaped flap 32 which is hingedly attached to the second portion 12. A free end 34 of the suture material 20 may be held in a notch 36 formed on the underside of the flap 32, so that the free end 34 may be conveniently placed for the veterinary surgeon's use.

Figure 5:
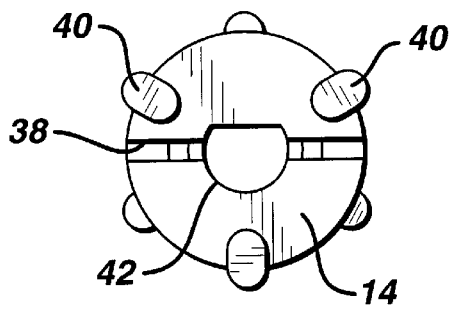
FIG. 5 is a plan view of a spool hub of a container according to the present invention.
Figure 6:
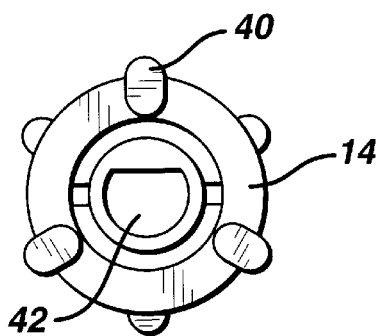
FIG. 6 is a reverse angle of the hub of FIG. 5.
Figure 4:
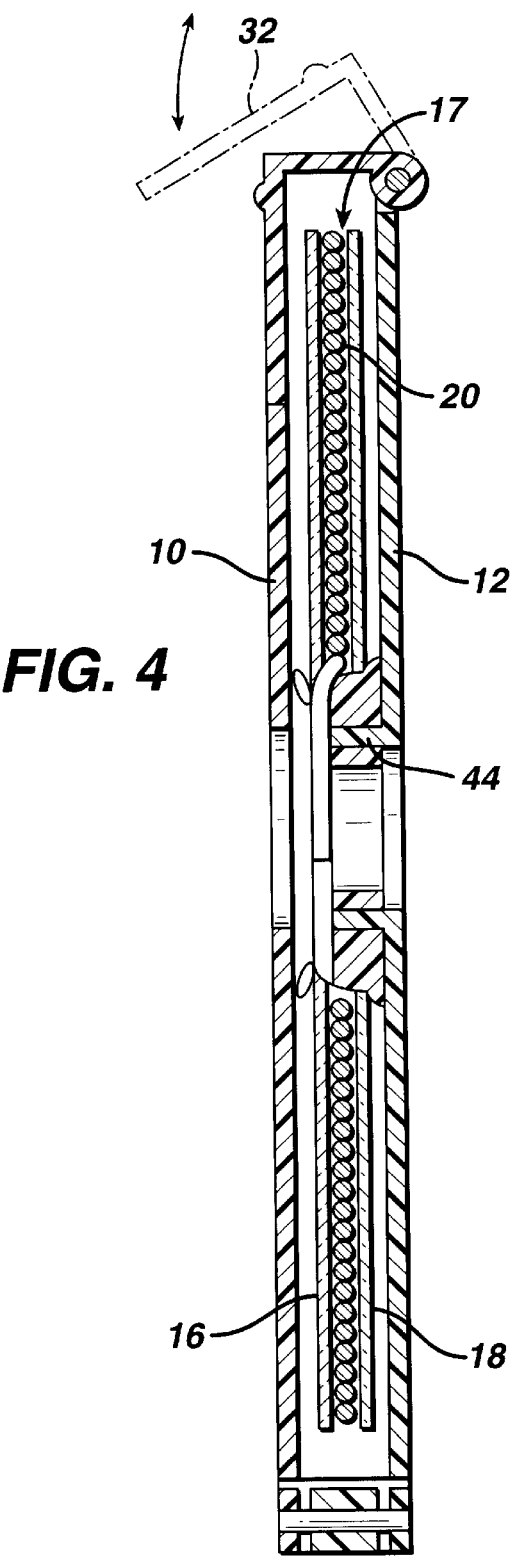
FIG. 4 is a section through a filled container according to the present invention.

Referring now to FIGS. 5 and 6, the hub 14 comprises a groove 38 adapted to accommodate an end of suture material 20, now shown. The hub 14 comprises clips 40 for securing the plastics discs 16, 18 to the hub 14 such that one of the plastic discs 16, 18 can secure the end of suture material 20 within the groove 38. The hub 14 further comprises a D-shaped hole 42 for engaging a D-shape drive means, now shown.

To load the container with suture material 20, the spool is first assembled. A first of the two plastics discs 16 is secured onto the hub 14, a suture end is then placed across the groove 38 and the second plastics disc 18 is pressed over the suture end and onto the hub over the clips 40 to secure the suture end in place by trapping the suture end within the groove 38. The spool is then placed onto a bearing 44 of the second portion 12. The spool with its attached suture may then be loaded by engaging the D-shaped hole 42 with a drive means to wind suture material 20 onto the spool. The first and second portions 10, 12 are then hingedly closed, and the free end 34 of the suture material is retained by the notch 36 on the flap 32. The flap 32 is then shut over the cut-away region 30. A container is thus provided with a suture wound onto a spool therein.

Alternatively, suture material may be wound onto the spool prior to mounting the spool in the container.

The suture material, the spool and the container may then be sterilized and packaged. The first and second portions 10, 12 are provided with a multitude of apertures 46 to allow ethylene oxide, or other sterilization medium to enter the container and to circulate around the inside of the container. These apertures are shown to be in a spiral formation to allow a uniform dispersion of ethylene oxide within the container.

After exposure of the suture and container to ethylene oxide for a suitable period of time, the sterilized container and suture is dried. Conveniently, drying is carried out first in a vacuum oven, and then at ambient pressure. Finally, the container is sealed within the outer envelope.

The present invention has been described above purely by way of example. Modifications in detail may be made within the scope of the invention as defined in the claims attached hereto.

I claim:

1. A suture container having a spool rotatably mounted therein, and a length of suture material wound on said spool, said container being wrapped in an outer bacterial-proof envelope, said container comprising a first portion and a second portion, the spool being rotatably mounted between the first and second portions, wherein the first and second portions are hingedly attached to each other, wherein the first and second portions are hingedly attached for relative movement about an axis substantially parallel to the axis of rotation of the spool, wherein the spool comprises a hub and two discs mounted thereon, wherein the discs are formed from transparent or translucent plastics material, wherein the hub is provided with means for receiving one end of a length of suture material, and wherein said means for receiving one end of a length of suture material comprises a slot or groove arranged substantially orthogonal to the axis of rotation of the hub.

* * * * *